United States Patent
Rodriguez

(10) Patent No.: US 10,213,364 B2
(45) Date of Patent: Feb. 26, 2019

(54) DELIVERY VEHICLE FOR DELIVERING BIOLOGICAL PRODUCTS TO A SURGICAL SITE AND METHODS THEREOF

(71) Applicant: Hospital for Special Surgery, New York, NY (US)

(72) Inventor: William Rodriguez, Garfield, NJ (US)

(73) Assignee: HOSPITAL FOR SPECIAL SURGERY, New York, NY (US)

( * ) Notice: Subject to any disclaimer, the term of this patent is extended or adjusted under 35 U.S.C. 154(b) by 440 days.

(21) Appl. No.: 14/061,292

(22) Filed: Oct. 23, 2013

(65) Prior Publication Data

US 2014/0112600 A1   Apr. 24, 2014

Related U.S. Application Data

(60) Provisional application No. 61/717,892, filed on Oct. 24, 2012.

(51) Int. Cl.
*A61J 1/10* (2006.01)
*A61M 31/00* (2006.01)

(52) U.S. Cl.
CPC .............. *A61J 1/10* (2013.01); *A61M 31/002* (2013.01)

(58) Field of Classification Search
CPC .... A61J 1/10; A61J 1/14; A61J 1/1443; A61J 1/1456; A61J 1/1468; A61M 31/002; A61M 35/00; A01N 25/18; A01N 25/08; A01N 25/34; B65D 5/00; C11B 9/00
See application file for complete search history.

(56) References Cited

U.S. PATENT DOCUMENTS

| | | | |
|---|---|---|---|
| 4,428,375 A * | 1/1984 | Ellman | A61B 17/12 606/151 |
| 5,376,101 A | 12/1994 | Green et al. | |
| 5,480,403 A | 1/1996 | Lee et al. | |
| D404,128 S | 1/1999 | Huebner | |
| 6,007,567 A | 12/1999 | Bonutti | |
| 8,197,509 B2 | 6/2012 | Contiliano et al. | |
| 8,267,973 B2 | 9/2012 | Humphrey | |
| 2009/0060975 A1 | 3/2009 | Teets et al. | |
| 2009/0222039 A1 | 9/2009 | Dreyfuss et al. | |
| 2010/0222750 A1* | 9/2010 | Cheng | 604/288.04 |
| 2011/0054408 A1* | 3/2011 | Wei | A61B 17/68 604/175 |
| 2013/0197530 A1* | 8/2013 | McKay | A61F 2/2846 606/94 |
| 2013/0226204 A1 | 8/2013 | Kumar | |
| 2014/0031795 A1* | 1/2014 | McKay | 604/518 |
| 2015/0025552 A1 | 1/2015 | Stoll | |

* cited by examiner

*Primary Examiner* — Benjamin Klein

(74) *Attorney, Agent, or Firm* — Kim Winston LLP

(57) ABSTRACT

A delivery vehicle for delivering biological products to a surgical site is provided that includes a container for housing the biological product and a fastener that extends from the container for securing the container at a location adjacent to the surgical site. The container is a flexible container having an access that is moveable between an open position and a closed position prior to and after being secured to the surgical site.

24 Claims, 4 Drawing Sheets

DELIVERY VEHICLE FOR DELIVERING BIOLOGICAL PRODUCTS TO A SURGICAL SITE AND METHODS THEREOF

CROSS REFERENCE TO RELATED APPLICATIONS

The present application claims the benefit of priority pursuant to 35 U.S.C. § 119(e) of U.S. Provisional Patent Application No. 61/717,892, filed Oct. 24, 2012, the entire disclosure of which is hereby incorporated by reference herein.

BACKGROUND OF THE INVENTION

The present invention relates generally to a delivery vehicle for the delivery of any number of forms of biological products to a surgical site and methods thereof. In particular, the present invention relates to a delivery vehicle for delivering biological products to a surgical site in which the delivery vehicle is attached to the surgical site.

In conventional practice, surgical sites, whether they are arthroscopic, endoscopic or of an open surgery variety are closed via sutures or staples. It is also known that certain biological products aid in the healing and regenerative process of such surgical sites. To take advantage of such biological products in aiding in the regenerative process of surgical sites, conventional practice is to coat or cover standard sutures with such biological products in an effort to deliver the biological products to the surgical site. However, such a method of delivering biological products to a surgical site does not result in an effective amount of biological product being delivered, nor does it provide a means to deliver additional biological products after suturing, or the ability to adequately deliver high viscous biological compounds.

Thus, there is still a need for a delivery vehicle that delivers biological products to a surgical site and addresses the foregoing deficiencies noted above. Such deficiencies are satisfied by the delivery vehicle of the present invention.

BRIEF SUMMARY OF THE INVENTION

In accordance with a preferred embodiment, the present invention provides for a delivery vehicle for delivering biological products to a surgical site. The delivery vehicle includes a flexible container and a fastener. The flexible container houses a biological product and includes an access that is moveable between an open position and a closed position. The fastener extends from the flexible container for securing the flexible container adjacent to the surgical site. The flexible container is moveable between open and closed positions when the fastener is secured to tissue about the surgical site.

In accordance with another preferred embodiment, the present invention provides a system for enhancing biological processes. The system includes a porous container, a high viscous biological product and a fastener. The porous container houses the high viscous biological product and has an access that is movable between an open position and a closed position. The fastener extends from the porous container for securing the porous container adjacent to a surgical site. The porous container is moveable between an open position and a closed position when secured adjacent to the surgical site.

In accordance with yet another preferred embodiment, the present invention provides a method of enhancing the delivery of a biological or pharmaceutical agent to a surgical site. The method includes the steps of providing a porous container having a fastener and securing a biological or pharmaceutical agent within the porous container. The method further includes the steps of introducing the porous container housing the biological product to the surgical site and securing the porous container to a location adjacent the surgical site. Finally, the method includes refilling the porous container with the biological or pharmaceutical agent after a predetermined period of time.

BRIEF DESCRIPTION OF THE SEVERAL VIEWS OF THE DRAWINGS

The foregoing summary, as well as the following detailed description of the preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Reference will now be made in detail to the preferred embodiments of the present invention illustrated in the accompanying drawings. Wherever possible, the same or like reference numbers will be used throughout the drawings to refer to the same or like features. It should be noted that the drawings are in simplified form and are not drawn to precise scale. In reference to the disclosure herein, for purposes of convenience and clarity only, directional terms such as top, bottom, above, below and diagonal, are used with respect to the accompanying drawings. Such directional terms used in conjunction with the following description of the drawings should not be construed to limit the scope of the invention in any manner not explicitly set forth. Additionally, the term "a," as used in the specification, means "at least one." The terminology includes the words above specifically mentioned, derivatives thereof, and words of similar import.

Figure 1A:
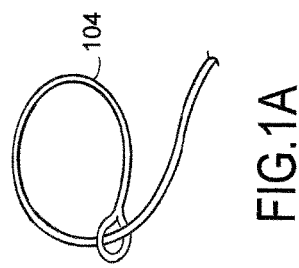
FIG. 1A is a perspective view of a fastener in accordance with the embodiment of FIG. 1.
Figure 2:
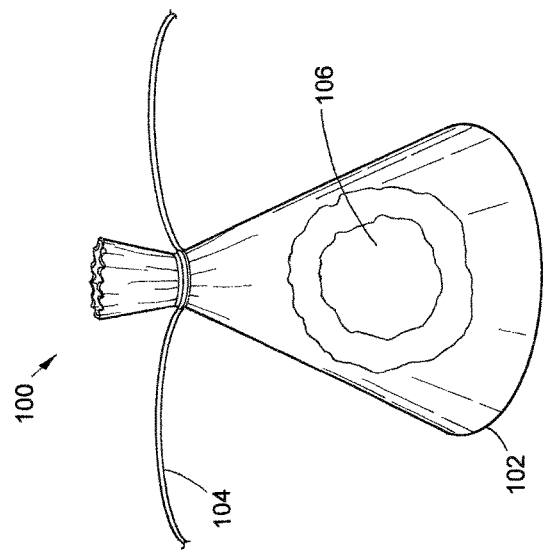
FIG. 2 is a perspective cutaway view of the delivery vehicle of FIG. 1 in a closed position.
Figure 1:
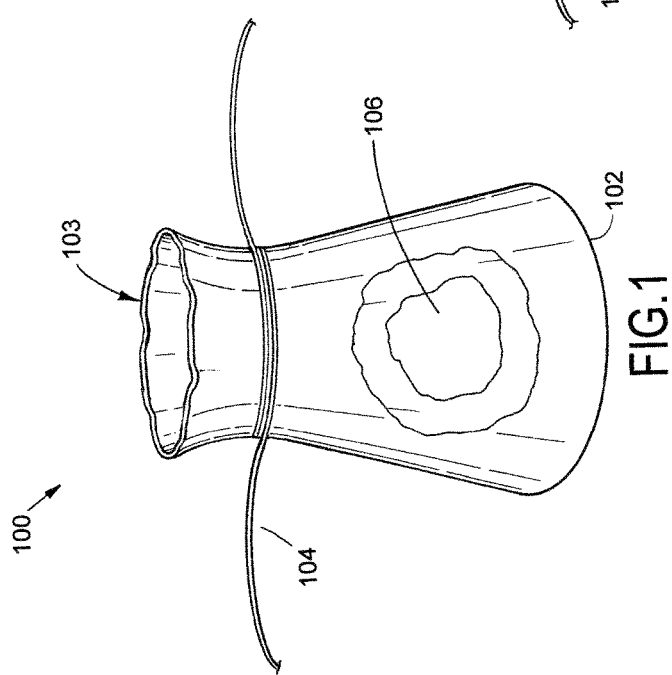
FIG. 1 is a perspective cutaway view of a delivery vehicle having a container in an open position in accordance with a preferred embodiment of the present invention.
Figure 4:
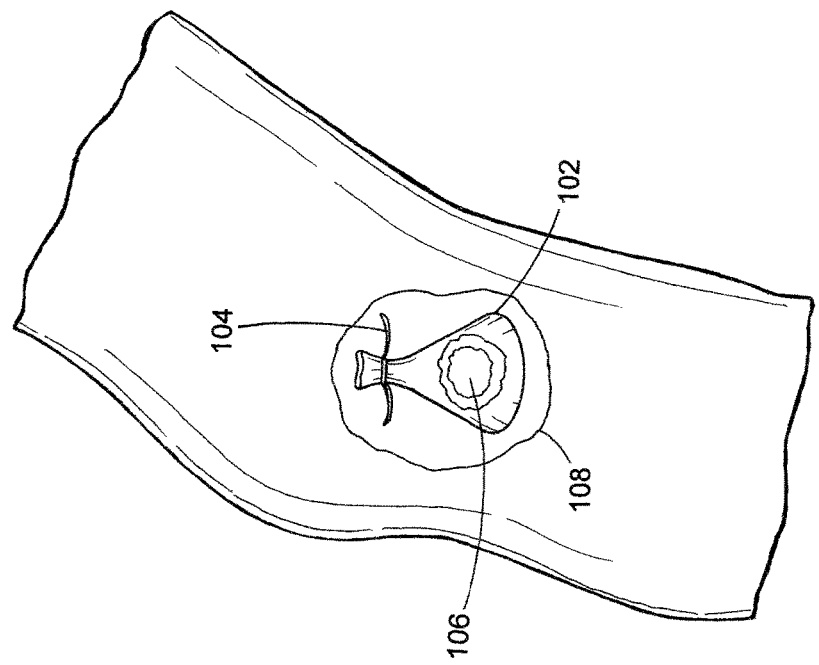
FIG. 4 is a perspective cutaway view of the delivery vehicle of FIG. 1 secured to a surgical site.

Referring to FIGS. 1, 2 and 4, in accordance with a preferred embodiment, the present invention provides a delivery vehicle 100 for delivering one or more biological products 106 to a surgical site 108 (FIG. 4). The delivery vehicle 100 includes a container 102, and a fastener 104 extending from the container 102. The delivery vehicle further includes a biological product 106 housed within the container 102 e.g., a high viscous biological product.

Referring to FIG. 1, the container 102 is a flexible container 102 that allows the flexible container 102 to conform its shape to any surface against which the flexible container 102 engages, such as a tissue surface. The flexible container 102 can be made e.g., from a planar sheet or nonplanar sheet of porous film, such as water soluble and insoluble porous films and biocompatible porous films. Such porous films are known in the art and a detailed description of them is not necessary for a complete understanding of the present invention. Thus, the flexible container can be configured as a porous container having a planar sheet of porous film or flexible porous film.

The flexible container 102 is preferably configured, as shown in FIGS. 1 and 2, and includes an access or opening 103 that is movable between an open position (FIG. 1) and a closed position (FIG. 2). In the open position, a user can deposit the biological product 106 within the flexible container 102. In the closed position, the biological product 106 is secured within the flexible container 102. As discussed further below, the flexible container 102 is movable between open and closed positions prior to the flexible container 102 being secured to the surgical site 108 and after the flexible container 102 is secured to the surgical site 108.

Figure 3:
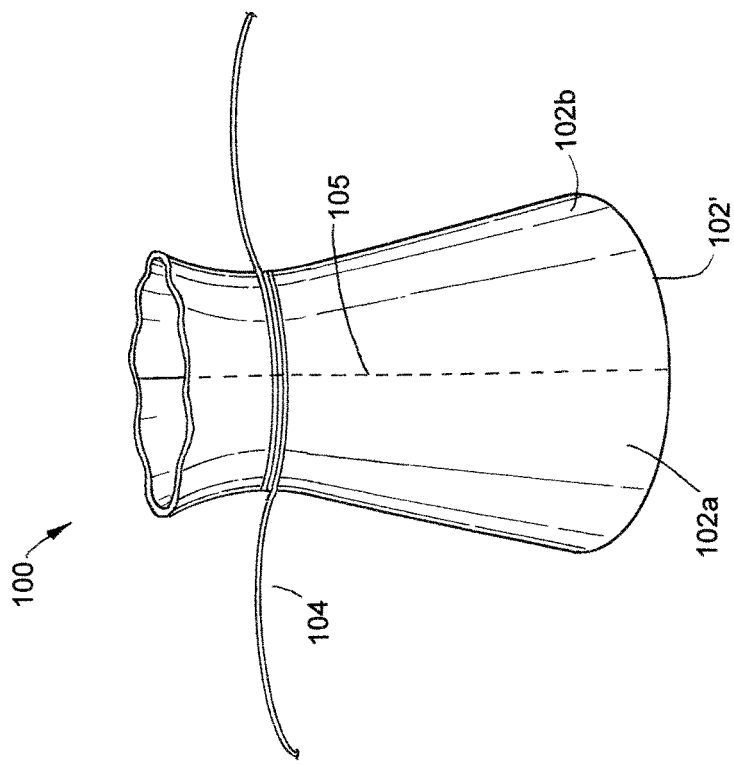
FIG. 3 is a perspective view of a delivery vehicle having a container with first and second compartments in accordance with another preferred embodiment of the present invention.

Referring to FIG. 3, in accordance with another aspect of the present invention, the flexible container 102' (e.g., a porous container) can be configured with at least a first compartment 102a and a second compartment 102b allowing for the storage of one or more different biological products 106 in each compartment. Additionally, the flexible container 102' can be configured with a plurality of compartments, such as three, four and five compartments. The additional compartments can be formed by a wall segment 105 that separates the first and second compartments 102a, 102b. The wall segment 105 can be a porous wall segment or a non-porous wall segment. The wall segment 105 can also be a dissolvable wall segment that dissolves to allow the biological products within the first and second compartments 102a, 102b to come together or mix after the delivery vehicle is attached to the surgical site.

The first compartment 102a can be formed from a first porous material having a first rate of diffusion through the first porous material and the second compartment 102b can be formed from a second porous material having a second rate of diffusion through the second porous material that is different from the first rate of diffusion. The first porous material is different from the second porous material. Having first and second compartments 102a, 102b formed from different porous materials having different rates of diffusion allows for the controlled release of biological products at differing rates. This can be a significant advantage e.g., when the need for a fast acting agent in combination with a slow sustained releasing agent is necessary.

The fastener 104 extends from the flexible container 102, as shown e.g., in FIG. 1. The fastener 104 is used to secure the flexible container 102 to the surgical site 108 or to a position adjacent the surgical site 108. For example, the fastener 104 can fasten the flexible container 102 to tissue at an incision point of the surgical site 108 or adjacent the incision point of the surgical site 108.

The fastener 104 can be any fastener suitable for the intended purpose of the present invention for fastening or introducing the delivery vehicle 100 to tissue. For example, the fastener 104 can be a suture, a wire, a clip, a plate, a screw, a pin, a washer, a prosthesis, a suture anchor or combinations thereof, such as those disclosed e.g., in U.S. Pat. Nos. 6,007,567; 8,197,509; 5,480,403; D404,128; 8,267,973; and 5,376,101, the entire disclosures of which are hereby incorporated by reference in their entirety.

Preferably, the fastener 104 is attached to or adjacent to the access or opening 103 of the flexible container 102. More preferably, the fastener 104 is configured to open and close the opening 103 of the flexible container 102 or allow the opening 103 to be opened and closed thereby forming a closable pouch container. This can be accomplished in a number of ways depending upon the type of fastener 104. For example, when the fastener 104 is a suture, the suture can be weaved through the walls of the flexible container 102 forming a draw-string pouch flexible container having one end of the suture looped through a looped end of the suture (see FIG. 1A). However, when the fastener is a pin (not shown), the pin can be inserted through opposing ends of the opening of the flexible container and pinned to soft or hard tissue, such as bone, to effectuate a closure of the opening 103.

The fastener 104 is also configured to allow the flexible container 102 to move the access between open and closed positions after the flexible container 102 is secured to tissue. That is, e.g., the pin fastener can be moved in and out of the tissue to effectuate a subsequent opening and closing of the flexible container 102 after a period of time from which the flexible container 102 is initially secured thereto. In the case of a suture fastener, the looped suture configuration allows for the flexible container 102 to be opened and closed a plurality of times after the flexible container 102 is secured to the tissue.

In sum, the fastener 104 is configured for multiple purposes. That is, the fastener 104 is used to close the open end of the flexible container 102 so that the biological product 106 is completely secured therein. Additionally, the fastener 104 is used to attach the flexible container 102 to an area adjacent to the surgical site 108 and maintain the container 102 in that position so that biological product 106 is effectively delivered directly to the surgical site 108. Furthermore, the fastener 104 allows a user to open and close the flexible container 102 after it is secured to a surgical site 108. The foregoing features of the present invention advantageously leads to a reduction in wasted biological product 106 that escapes to other parts of the body and concentrates the release of the biological product 106 to the surgical site 108 to maximize efficiency and efficacy of the biological product 106.

The biological product 106 can be any biological product 106 that is capable of being housed within a porous container. Preferably, the biological product 106 is a viscous or highly viscous biological product 106. For example, the biological product 106 can be a mineral rich compound, such as protein rich plasma, platelet rich plasma, or other blood components or blood fractions isolated so as to be containable within a porous container 102 or of a semifluid or semisolid consistency. Exemplary biological products applicable to the present invention include, but are not limited to, liposomes, stem cell fractions, bone marrow, mesenchymal cells, and conditioned plasma. Additional biological products 106 are applicable to the present invention provided that such biological products 106 are capable of being housed or contained within the flexible container 102. More preferably, the biological product 106 is an autologous compound isolated to a semifluid or semisolid consistency or state.

The biological product 106 used in connection with the present invention is preferably in a non-liquid state such that it can be manipulated and easily housed or contained within the flexible container 102. However, the biological product 106 can also be in a liquid form that is supported on a carrier, such as a collagen matrix or other biocompatible and/or bioabsorbable matrix.

Figure 5:
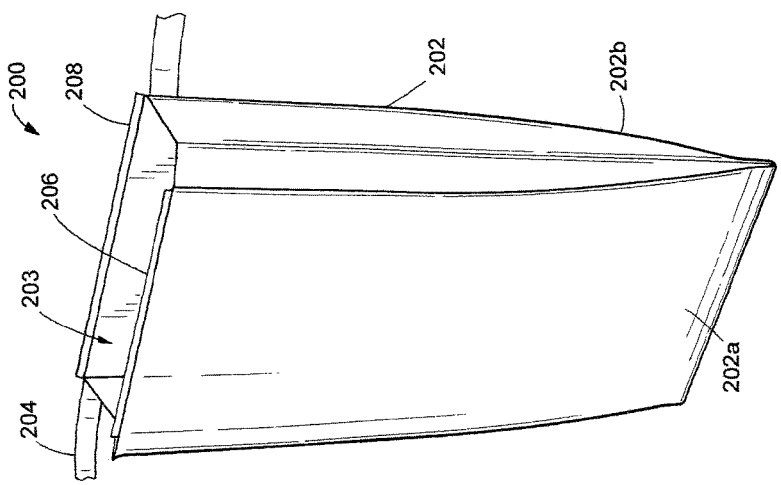
FIG. 5 is a perspective view of a delivery vehicle having a container in accordance with yet another preferred embodiment of the present invention.

Referring to FIG. 5, in accordance with another aspect of the present invention, the flexible container 202 can be formed as shown (FIG. 5) having an opening 203. The flexible container 202 also includes a substantially planar front side 202a and a substantially planar rear side 202b. The flexible container 202 can be completely formed from a porous material, such as a porous film. Alternatively, the flexible container 202 can be configured with the front side 202a formed from a porous material and the rear side 202b formed from a nonporous material. As such, the rear side 202b provides a first nonporous wall surface and the front side 202a provides a second porous wall surface forming the flexible container.

The fastener 204 is configured to extend from the flexible container and orient the front side 202a or the second porous wall surface to facingly engage with tissue to which the flexible container is secured to adjacent the surgical site i.e., when the fastener 204 is secured to the tissue. For example, when the fastener 204 is a suture, the suture is configured along a rear side 202b of the flexible container opening 203 such that when the suture is tied, connected, or secured to the tissue, the front side 202a is facing and in direct contact with the tissue which is targeted for exposure with the biological product 106 contained within the flexible container 202.

In this configuration, when the suture secures the flexible container 202 to tissue, the suture also acts to move the flexible container 202 to the closed position i.e., to close the opening 203 of the flexible container 202. Thus, when secured to tissue about a surgical site, the flexible container 202 has its porous wall surface 202a engaging the targeted tissue for exposure to the biological product 106 that diffuses out through the porous wall surface 202b, while the nonporous wall precludes the biological product 106 from diffusing out of the flexible container 202 to a nontargeted tissue region.

Figure 6:
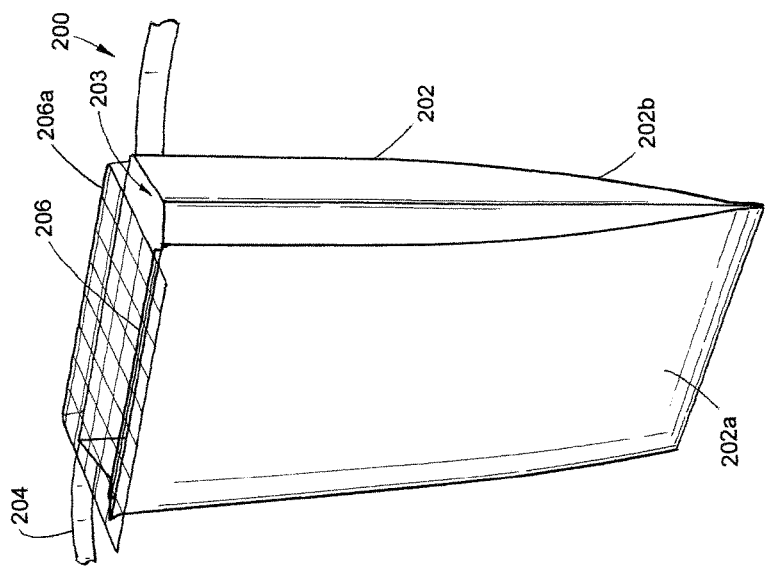
FIG. 6 is a perspective view of the delivery vehicle of FIG. 5 having a filter cover.

Referring to FIGS. 5 and 6, the flexible container 202 can optionally include a filter 206. The filter 206 can line one or more walls of the flexible container 202 to filter material diffusing through the flexible container wall. Alternatively, the filter 206 can serve as a closure flap 206a for covering the opening 203 of the flexible container 202 when the flexible container 202 is secured to tissue.

Referring back to FIG. 5, the flexible container 202 may also be configured to include a radiopaque marker 208. The radiopaque marker 208 can be positioned along any portion of the flexible container 202 or the fastener 204. Preferably, the radiopaque marker 208 is positioned along or adjacent to the opening 203 of the flexible container 202 such that the opening 203 can be identified via a radiograph of the flexible container 202. As an alternative to the radiopaque marker 208, the flexible container 202 can be configured with a magnetic resonance imaging (MRI) marker, a sonogram marker, or any other marker that is detectable via a diagnostic instrument.

Figure 7:
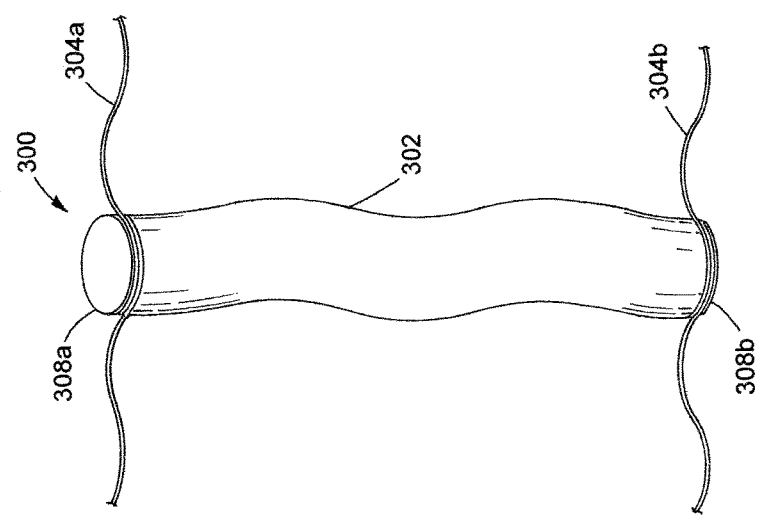
FIG. 7 is a perspective view of a delivery vehicle having a container in accordance with a further preferred embodiment of the present invention.

Referring to FIG. 7, in accordance with another embodiment, the present invention provides for a delivery vehicle 300 having a flexible container 302 configured as shown (FIG. 7). In particular, the flexible container 302 is formed to have a hollow substantially cylindrical shape. While a hollow cylindrical shape is preferred, the flexible container 302 can be of any shape that is elongated such as a parallel pipe or a triangular cross sectioned pipe. The flexible container 302 has an open first end 308a and an open second end 308b opposite the open first end 308a. However, the flexible container 302 can alternatively be configured to have only a single open end with the opposite end being a permanently closed end.

The flexible container 302 further includes a first fastener 304a about the open first end 308a of the flexible container 302 and a second fastener 304b about the open second end 308b opposite the open first end 308a. The fasteners 304a, 304b serve to close and open the first and second open ends 308a, 308b and for securing the flexible container 302 to tissue. Similar to the above described embodiments of the flexible container 102, the flexible container 302 is similarly configured to move between open and closed ends when secured to tissue.

The delivery vehicle 300 advantageously provides for an elongated delivery vehicle that can provide for the delivery of a biological product across a length of tissue, e.g., to match an elongated incision site. The delivery vehicle 300 also provides for a pair of fasteners 304a, 304b for securing the delivery vehicle 300 to tissue in a variety of positions, such as a surgical site or a bone fracture site.

Referring back to FIGS. 1 and 2, the flexible container 102 (and flexible containers 202 and 302) can be completely formed out of water soluble porous materials such that the flexible container 102 can be completely resorbed by the body. However, the flexible container 102 can alternatively be formed out of nonresorbable porous materials so that the flexible container 102 can serve as a semi-permanent delivery vehicle positioned at a predetermined or specific site within the body. Additionally, the flexible container 102 can have certain walls formed out of a completely resorbable porous material while having other walls formed out of a nonresorbable material. For example, the flexible container 202 (FIG. 5) can have its porous wall formed out of a water soluble porous material while its nonporous wall is formed out of a nonresorbable porous material.

Further, the flexible container 102 itself can be impregnated or coated with one or more biological products or pharmaceutical agents, such as an anesthetic or antibiotic.

One of the advantages of the present invention is that the flexible container 102 (e.g., a porous container) includes an access that is moveable between open and closed positions while being secured to tissue adjacent a surgical site i.e., a location adjacent the surgical site. This feature advantageously provides a user the ability to refill or recharge the flexible container 102 with additional or alternative biological products thereby giving a medical practitioner additional treatment options for patients having the flexible container 102.

Another advantage of the present invention is that the foregoing embodiments of the delivery vehicle 100, 200, 300 provide a system for enhancing biological processes of the body when the biological product 106 includes products for enhancing such processes, such as regenerative processes. That is, the system includes a flexible container, as described in any of the above embodiments having a biological product 106, such as a regenerative process biological product. Preferably, the biological product 106 is a protein rich plasma or a platelet rich plasma and more preferably, autologous protein rich plasma or autologous platelet rich plasma.

Figure 8:
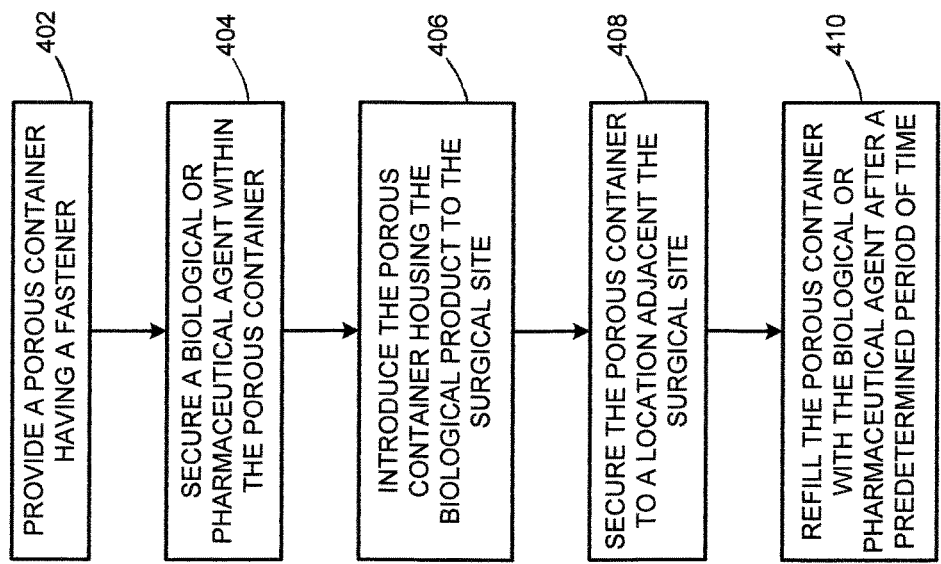
FIG. 8 is a flowchart of a method in accordance with yet another preferred embodiment of the present invention.

Referring to FIG. 8, in accordance with another preferred embodiment, the present invention provides for a method of enhancing the delivery of a biological or pharmaceutical agent to a surgical site 108. The method includes the step of providing a porous container 102 having a fastener 104, as described in any of the above embodiments (Step 402). Then securing the biological or pharmaceutical agent within the porous container 102 (Step 404). Thereafter, the method includes introducing the porous container housing the biological or pharmaceutical agent to the surgical site 108 (Step 406). The step of introducing the porous container 102 can be accomplished in a variety of ways, such as with a needle, a needle holder, an arthroscopic, an endoscopic, or via open surgery.

The method further includes the step of securing the porous container 102 to a location adjacent the surgical site 108 (Step 408). Moreover, in securing the porous container, the fastener is connected to tissue adjacent the surgical site. The location adjacent to the surgical site 108 can be soft tissue, such as skin, muscle, etc. or hard tissue such as bone. Additionally, when the porous container includes first and second compartments, the method includes securing a first biological or pharmaceutical agent within the first compartment and securing a second biological or pharmaceutical agent within the second compartment. The second biological or pharmaceutical agent can be different or the same as the first biological or pharmaceutical agent.

Thereafter, the method includes refilling the porous container 102 with the biological or pharmaceutical agent after a predetermined period of time (Step 410). For example, the general rate of diffusion through the porous container 102 will be generally known, thus the predetermined time period can be the time period in which a medical practitioner knows approximately when the biological or pharmaceutical agent will completely diffuse out through the porous container 102 (i.e. when the porous container 102 will be emptied).

Moreover, when the porous container has a first nonporous wall surface and a second porous wall surface, the method further includes orienting the second porous wall surface to be in facing engagement with a tissue and securing the porous container to the tissue with the second porous wall in facing engagement with the tissue.

The biological agent can be any of the above described biological products 106. The pharmaceutical agent can be any pharmaceutical agent capable of being housed within a porous container 102 or which has a semifluid or semisolid nature or state. Preferably, the pharmaceutical agent is an antibiotic compound.

It will be appreciated by those skilled in the art that changes could be made to the embodiments described above without departing from the broad inventive concept thereof. For example, additional components and steps can be added to the system and method for delivering biological products to a surgical site. It is to be understood, therefore, that this invention is not limited to the particular embodiment disclosed, but it is intended to cover modifications within the spirit and scope of the present invention as defined by the appended claims.

I claim:

1. A delivery vehicle for delivering biological products to a surgical site comprising:
a sterile flexible porous film container for housing a biological product, the sterile flexible porous film container having:
an access that is moveable between an open position and a closed position,
a first compartment in fluid communication with the access, and
a second compartment in fluid communication with the access;
a filter covering the access; and
a fastener for securing the sterile flexible porous film container adjacent to the surgical site,
wherein the sterile flexible porous film container is moveable between open and closed positions via the fastener.

2. The delivery vehicle of claim 1, wherein the fastener extends from the flexible container.

3. The delivery vehicle of claim 1, wherein the fastener is a suture, a wire, a clip, a plate, a screw, a pin, a washer, a prosthesis, a suture anchor or combinations thereof.

4. The delivery vehicle of claim 1, wherein the first compartment is formed from a first flexible porous film material having a first rate of diffusion through the first flexible porous film material and the second compartment is formed from a second flexible porous film material having a second rate of diffusion through the second flexible porous film material.

5. The delivery vehicle of claim 1, wherein the flexible porous film container has a first nonporous wall surface and a second porous wall surface, and wherein the fastener is configured to extend from the flexible porous film container to orient the second porous wall surface to facingly engage a tissue to which the flexible container is secured to adjacent the surgical site.

6. The delivery vehicle of claim 1, wherein the flexible porous film container houses a high viscous biological product selected from the group consisting of protein rich plasma, platelet rich plasma, a mineral rich compound, and an autologous compound.

7. The delivery vehicle of claim 1, wherein the flexible porous film container further includes a substantially planar front wall, a substantially planar rear wall, and expandable side walls extending substantially transverse to a major plane of the substantially planar front and rear walls.

8. The delivery vehicle of claim 1, wherein the first compartment forms part of the access and the second compartment forms part of the access, and wherein the sterile flexible porous film container houses a biological product.

9. The delivery vehicle of claim 7, wherein the access is a substantially rectangular-shaped access.

10. The delivery vehicle of claim 1, wherein the sterile flexible porous film container includes a diagnostic marker positioned adjacent the access.

11. The delivery vehicle of claim 1, wherein the sterile flexible porous film container is formed completely of a water soluble porous material.

12. The delivery vehicle of claim 1, wherein the sterile flexible porous film container is impregnated or coated with one or more biological products and/or pharmaceutical agents.

13. A system for enhancing biological processes comprising:
a sterile porous container formed from a porous film and configured to house a high viscous biological product, the sterile porous container having:
an access that is movable between an open position and a closed position,
a first compartment in fluid communication with and forming part of the access, and
a second compartment in fluid communication with and forming part of the access; and
a filter covering the access; and a fastener extending from the sterile porous container for securing the sterile porous container adjacent to a surgical site, and configured to move the access between the open and closed positions.

14. The system of claim 13, wherein the fastener is at least one selected from the group consisting of a suture, a wire, a clip, a plate, a screw, a pin, a washer, a prosthesis, and a suture anchor.

15. The system of claim 13, wherein the porous container includes a planar sheet of flexible porous film and the fastener is connected to the porous film forming a drawstring pouch porous container.

16. The system of claim 13, wherein the first compartment is formed from a first porous material having a first rate of diffusion through the first porous material and the second compartment is formed from a second porous material having a second rate of diffusion through the second porous material.

17. The system of claim 13, wherein the high viscous biological product is protein rich plasma, platelet rich plasma, a mineral rich compound, an autologous compound, or combinations thereof.

18. The system of claim 13, wherein the porous container further includes an expandable side wall extending between a substantially planar front side and a substantially planar back side, wherein the expandable side wall includes planar side wall segments.

19. A method of enhancing the delivery of a biological or pharmaceutical agent to a surgical site comprising:
using a sterile flexible porous film container that includes:
an access moveable between an open position and a closed position, and
a fastener for securing the sterile flexible porous film container adjacent to the surgical site, wherein the sterile flexible porous film container is moveable between open and closed positions via the fastener;
securing a biological or pharmaceutical agent within the sterile flexible porous film container via the fastener;
introducing the sterile flexible porous film container housing the biological product to the surgical site;
securing the sterile flexible porous film container to a location adjacent the surgical site via the fastener;
opening the access via the fastener while the sterile flexible porous film container is secured to the surgical site; and
refilling the sterile flexible porous film container via the access with the biological or pharmaceutical agent after a predetermined period of time.

20. The method of claim 19, wherein in the securing step, the fastener is secured to a tissue adjacent the surgical site.

21. The method of claim 19, wherein the pharmaceutical agent is an antibiotic.

22. The method of claim 19, wherein in the introducing step, the flexible porous film container is introduced to the surgical site arthroscopically or endoscopically.

23. The method of claim 19, comprising the step of securing a first biological or pharmaceutical agent within the first compartment and a second biological or pharmaceutical agent within the second compartment.

24. The method of claim 19, wherein the flexible porous film container has a first nonporous wall surface and a second porous wall surface, and further comprising orienting the second porous wall surface to be in facing engagement with a tissue and securing the flexible porous film container to the tissue with the second porous wall in facing engagement with the tissue.

* * * * *